United States Patent [19]

Garito et al.

[11] Patent Number: 4,754,754
[45] Date of Patent: Jul. 5, 1988

[54] ELECTROSURGICAL HANDPIECE FOR BLADES AND NEEDLES

[76] Inventors: Jon C. Garito, 264 Hedge Ln., Hewlett Harbor, N.Y. 11577; Alan G. Ellman, 1 Auerbach Ln., Lawrence, N.Y. 11516

[21] Appl. No.: 925,530

[22] Filed: Oct. 28, 1986

Related U.S. Application Data

[63] Continuation of Ser. No. 642,521, Aug. 20, 1984, abandoned.

[51] Int. Cl.$^4$ ............................................. A61B 17/39
[52] U.S. Cl. ........................... 128/303.14; 128/303.17; 128/303.19
[58] Field of Search .......................... 128/303 R, 303.1, 303.13–303.14, 128/303.17–303.19, 800, 734, 737, 739, 741, 776–777, 784; 604/20

[56] References Cited

U.S. PATENT DOCUMENTS

| | | | |
|---|---|---|---|
| 2,437,697 | 3/1948 | Kalom | 128/737 |
| 2,516,882 | 8/1950 | Kalom | 128/737 |
| 2,522,052 | 9/1950 | Logan et al. | 128/734 |
| 2,616,415 | 11/1952 | Kirby et al. | 128/737 |
| 3,648,001 | 3/1972 | Anderson et al. | 128/303.14 X |
| 3,746,814 | 7/1973 | Lackey et al. | 128/800 X |
| 3,804,096 | 4/1974 | Gonser | 128/303.14 |
| 3,995,644 | 12/1976 | Parsons | 128/784 |
| 4,014,343 | 3/1977 | Esty | 128/303.17 X |
| 4,034,761 | 7/1977 | Prater et al. | 128/303.17 X |
| 4,481,057 | 11/1984 | Beard | 128/303.14 X |
| 4,545,375 | 10/1985 | Cline | 128/303.14 |

Primary Examiner—William E. Kamm
Assistant Examiner—Angela D. Sykes
Attorney, Agent, or Firm—Rosen, Dainow & Jacobs

[57] ABSTRACT

A novel handpiece for use with electrosurgical equipment and adapted to receive a disposable scalpel blade having an elongated insulated handle having first and second ends with its second end having an opening to the handle interior, an insulated electrical wire coupled to the first end of the handle, an electrically conductive structure mounted within the handle at its second end and electrically connected to the wire, the structure including within the handle an elongated metal part having adjacent the handle second end a collet and having further removed from the second end an externally-threaded portion, the handle at its second end having a separable portion having on its interior an internally-threaded portion and configured such that the latter threadingly engages the externally threaded portion and when so engaged and rotated in one direction engages and tightens up on the collet, and when rotated in the opposite direction loosens up on the collet, the collet being constructed to receive and firmly hold a scalpel blade inserted therein by its flat side when the separable handle portion is rotated in one direction, the separable handle portion being configured to receive and surround the non-sharpened end of the scalpel blade so that the latter may be inserted into the collet on its interior through the opening at the handle second end.

12 Claims, 3 Drawing Sheets

U.S. Patent   Jul. 5, 1988   Sheet 3 of 3   4,754,754
FIG.7
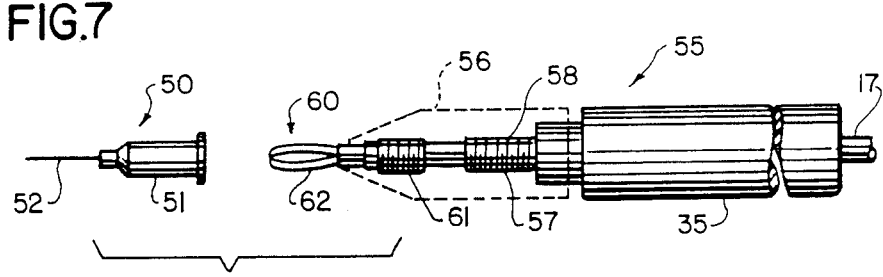
FIG.8
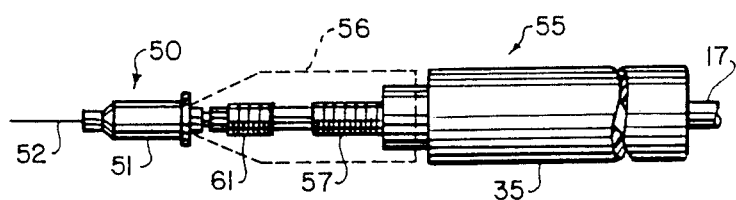
FIG.9
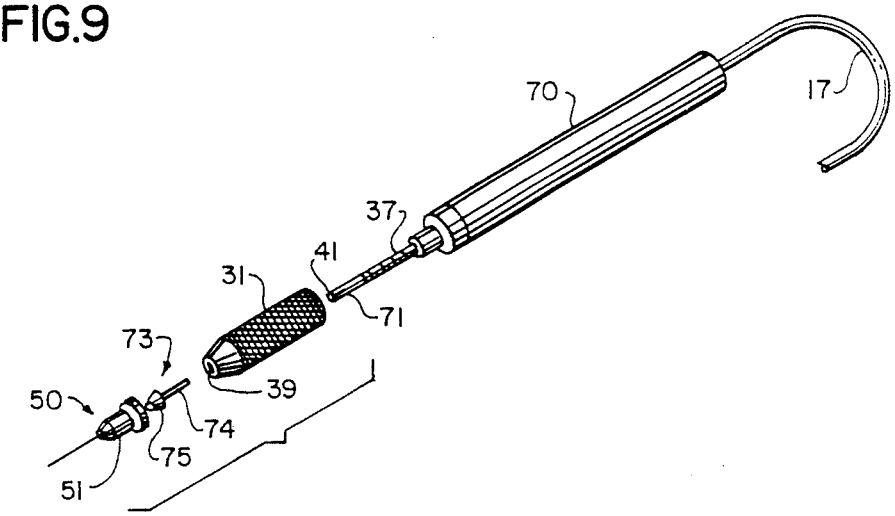
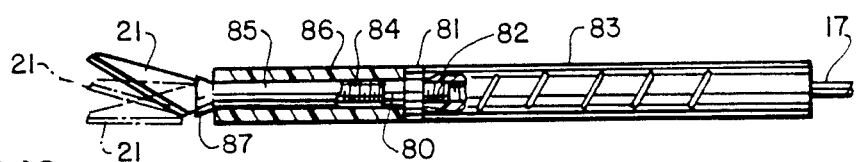
FIG.10

ELECTROSURGICAL HANDPIECE FOR BLADES AND NEEDLES

This is a continuation of application Ser. No. 642,521, filed Aug. 20, 1984 and now abandoned.

This invention relates to electrosurgery apparatus, and specifically to new handpieces or handpiece adaptors for receiving electrodes in the form of blades or needles.

BACKGROUND OF THE INVENTION

U.S. Pat. No. 3,730,188, whose contents are hereby incorporated by reference, describes electrosurgical apparatus for dental use, and describes one form of electrical circuit for generating radio-frequency (RF) currents with different waveform shapes to optimize tissue cutting, hemostasis, or both. Similar apparatus is employed in the medical and veterinarian fields. Different forms of the apparatus are available commercially from a number of suppliers.

In a typical commercial machine, a socket is provided connected to the RF generator on the machine front panel to receive an electrical plug connected at one end of an insulated wire, at the opposite end of which is provided a handpiece to be held by the dentist or physician. The handpiece is configured to receive a removable working electrode by which the RF currents can be applied to the patient's tissue for cutting or hemostasis. Typical electrodes commonly in use include needle shapes, wire circular or diamond loop shapes, ball shapes or blade shapes. These electrodes are custom designed for each machine and are thus expensive. In addition, the working end, usually of exposed metal at the tip, is elsewhere enclosed in an insulating layer, to avoid RF current leakage to the patient other than from the exposed tip. After use, the electrodes from the handpiece are sterilized for use with the next patient. Aside from the time wasted in the sterilization process, the latter reduces the usable lifetime of the electrode, thus requiring more frequent replacement, adding to the already high cost.

The trend, especially in the medical arts, is toward disposable instruments, which can be discarded after use. There already exist standard-sized disposable scalpel blades and needles available at low cost in sterilized packages, for use with non-electrosurgical hand instruments, but these will not fit into the available electrosurgical handpieces.

One supplier of medical electrosurgical equipment has attempted to fill this need by designing new electrosurgical equipment with a new handpiece adapted to receive disposable scalpel blades. But, the equipment is very expensive, and the disposable blades are not of the inexpensive variety available at low cost, but are custom-designed with internal heating elements regulated by the equipment, the regulated high temperature assumed by the blade during use producing as alleged hemostasis of blood vessels as they are cut. Thus the need for low cost equipment with low cost standard scalpel electrodes is not satisfied by this equipment. Moreover, the handpiece is not capable of receiving needle electrodes.

BRIEF SUMMARY OF THE INVENTION

The principal object of the invention is a novel handpiece that can be employed with existing commercially-available electrosurgery equipment and is adapted to receive existing low-cost commercially-available disposable scalpel blades or needles.

This and other objects and advantages of the invention as will appear hereinafter is achieved, in one embodiment, by configuring the handpiece with a collet type holder or chuck for receiving and holding or clamping a disposable scalpel blade in electrical connection with the RF current-carrying wire of the handpiece.

In another embodiment, an adaptor or coupling piece is provided to be mounted into the collet of a standard electrosurgical handpiece, the adaptor piece having an enlarged end to directly receive and support the hub of a standard disposable needle.

In still another embodiment, a novel electrosurgical handpiece is provided with an enlarged electrically conductive end to receive directly the hub of the standard disposable needle.

BRIEF DESCRIPTION OF DRAWINGS

The various embodiments of the present invention will now be described in greater detail with reference to the accompanying drawings,
Wherein:

FIG. 7 is a partly exploded view of a second embodiment of the invention for use with needles;

FIG. 8 shows the embodiment of FIG. 7 but with assembled needle;

FIG. 9 is an exploded, perspective view of a third embodiment also intended for use with needles.

FIG. 10 is a variant.

DETAILED DESCRIPTION OF PREFERRED EMBODIMENTS

Figure 1:
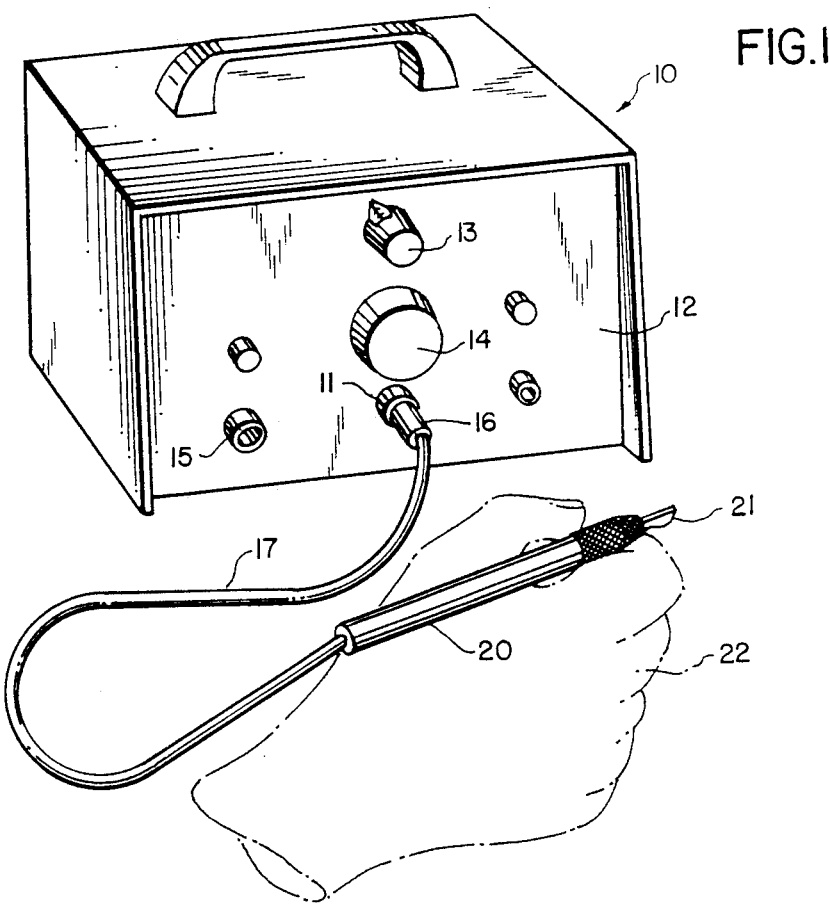
FIG. 1 is a schematic view showing a typical electrosurgical unit to which is connected one form of handpiece according to the invention.

Referring now to the drawing, FIG. 1 illustrates schematically a conventional form of electrosurgery equipment for dental, medical or veterinarian use, to which has been added one form of the novel handpiece of the invention. It comprises an apparatus or unit 10 which upon activation manually or by a foot control (not shown) generates RF currents accessible at a socket 11 on the front panel 12. The unit typically includes a switch 13 for controlling the waveforms of the RF currents, as described in the cited patent, and a switch 14 for controlling the intensity or amplitude of the currents, which may or may not be regulated. A socket 15 is usually provided for receiving an electrical plug connected to a grounding pad (not shown) which is attached to or held by the patient. Plugged into the RF output socket 11 is an electrical plug 16 to which is connected a long electrically insulated cable or wire 17, which in turn is permanently connected to one end of a handpiece 20 which at its opposite end contains the working electrode 21 depicted as a scalpel blade. The hand of the user (doctor or dentist) is shown at 22 holding the handpiece 20 for use on a patient.

Figure 2A:
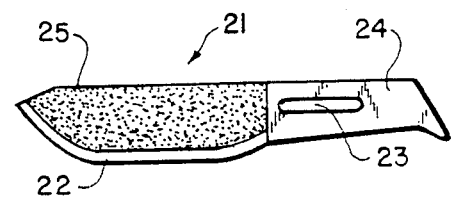
FIGS. 2A, 2B and 2C are side views of typical standard sized disposable blades.
Figure 2B:
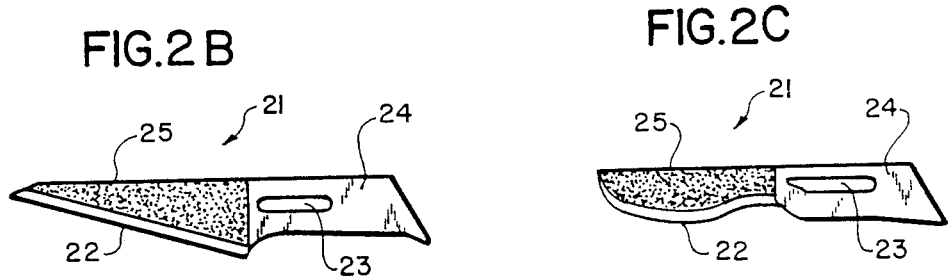
Figure 2C:
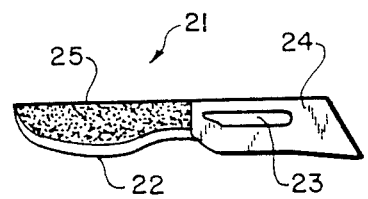

FIGS. 2A, 2B, and 2C illustrate standard forms of disposable scalpel blades which are available commercially in sterilized packages from a number of suppliers. Different shapes of blades defined by standard numbers are available. FIG. 2 illustrates three popular shapes numbered, respectively, Nos. 10, 11 and 15. The blade itself 21 is typically constructed of flat stainless steel with a surgically sharpened edge 22. The rear part of the blade 24 is typically provided with a slot 23 whereby the blade can be removably mounted on a manual handle for use by the physician in a non-electrosurgical procedure. The slot 23 is not used for mounting purposes in the electrosurgical handpiece of the invention. The front part of the blade 21, which protrudes from the handpiece is preferably coated, as shown at 25, with an electrically insulating coating which covers all of the exposed blade except for the sharpened edge 22. TEFLON is a preferred material for this coating, but other plastics can also be substituted. The standard blades are not coated as described, since they are intended for non-electrosurgical applications. The non-coated blades can also be used in the invention, but the addition of the coating 25 is preferred to avoid leakage of RF currents to the patient except at the exposed sharpened edge. The addition of the plastic coating contributes only a small extra cost to the manufacture of the blades.

Figure 3:
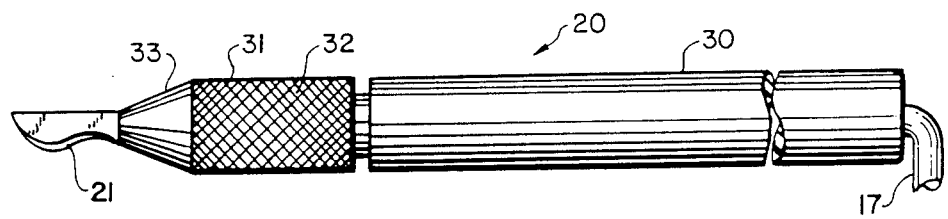
FIG. 3 is an enlarged side view of the handpiece of FIG. 1.

The handpiece 20 with mounted blade 21 is illustrated in FIG. 3. It comprises a straight elongated handle 30, constituted of electrically insulating material, for example, of the plastic BAKELITE. The forward portion, in this embodiment, is constituted of a removable cap or sleeve 31, knurled 32 on the outside for easier handling. The front is tapered 33 to avoid blocking the user's view of the electrode 21.

Figure 4:
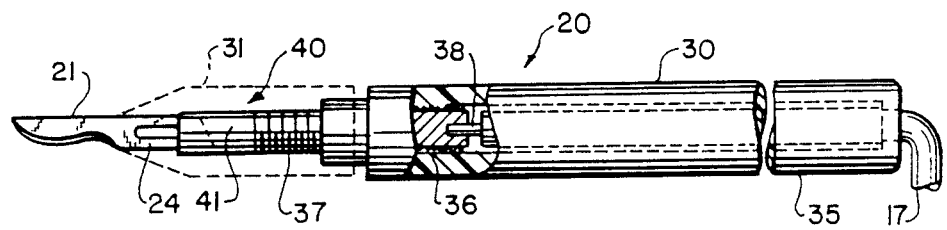
FIG. 4 is a view similar to FIG. 3 but with parts cut away or omitted to show interior details.
Figure 5:
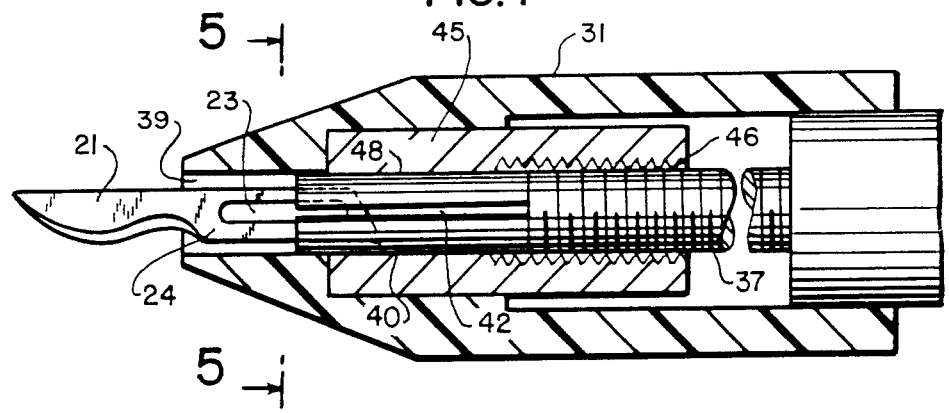
FIG. 5 is a partly cross-sectional view of the front part of the handpiece of FIG. 4 showing further details.
Figure 6:
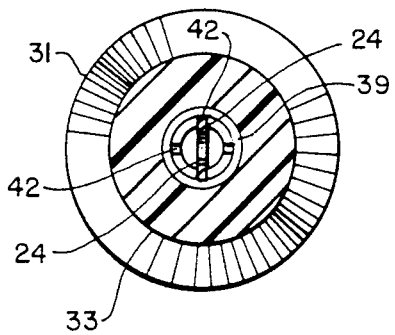
FIG. 6 is a cross-sectional view along the line 5—5 of FIG. 5.

The internal construction of the handpiece 20 is depicted in FIGS. 4–6. The rear portion 35 of the handle is hollow to allow entrance of the RF cable 17. A centrally-disposed wall 36 supports an externally threaded elongated thin bushing or rod 37, preferably of brass, having at one end a small cavity 38 into which is soldered the internal wire conductor of the cable 17. The rod 37 is of uniform diameter and is threaded over about two-thirds of its length. It is glued in place in the wall 36. The front end 40 of the rod, which is not threaded, functions as a collet or chuck, achieved by boring an axial hole 41 along its center, and then providing slits 42 in the side walls thus formed. Four slits are adequate for this purpose, and the slits 42 are preferably provided as two pairs of vertically and horizontally aligned slits, achieved by locating the slits 90° apart as radial-extending slits (see FIG. 6).

The front removable cap 31 is hollow with a front bore 39 wide enough to receive the rear or mounting end 24 of the blade 21. As shown in FIG. 5, the blade rear end 24 is pushed through the bore 39 and into the two vertically aligned slits 42 of the collet 40, which slits are wide enough to accommodate the thickness of the flat blade. This action is assisted by the use of brass for the collet, which makes the slitted end slightly flexible and resilient. On the interior of the cap 31 is mounted a metal insert 45 which has an internal thread 46 adapted to threadingly engage the externally threaded portion of the rod 37, when the cap 31 is placed over the blade and rotated clockwise to engage the threads. As the cap 31 advances toward the handle portion 35, during this rotation, an internal taper 48 on the insert 45 engages and cams inward on the collet slitted end 40, closing down the slits 42 and clamping the blade end 24 firmly in the collet 40. When the cap is rotated counterclockwise, the cap 31 retracts and the insert 45 disengages from the collet 40. The slight natural resilience in the rod end 40 causes the fingers formed by the slits on the collet to return to their unstressed position and the blade end 24 can thus be readily removed by pulling from the collet 40 after use. Note that the slot 23 in the blade mounting portion 24 is not used to mount in the handpiece, yet the blade is firmly held in the handpiece.

The embodiment so far described is used with disposable blades, and cannot in its present form be used to support a disposable needle 50, one standard form of which, also available commercially in various sizes, is depicted in FIGS. 7 and 9. Though the needle diameter and length may vary in the different sizes, the mounting hub is standardized, and comprises a slightly flanged hollow hub 51 from which the needle point 52 protrudes. In the second embodiment now to be described with reference to FIGS. 7 and 8, a modified handpiece 55 is employed which is adapted only to support a disposable needle. The same reference numerals are employed as in the first embodiment to designate the same or similar elements. In this second embodiment, the handpiece is designated 55, having the usual handle 35 and connecting cable 17. In this case, the front cap 56 is not removable, but is permanently fixed in place as by gluing. A modified bushing or rod 57 is employed, which is anchored as before in the center wall of the handle. The rod 57 is still shown threaded at 58 for better anchoring to the wall, but need not be, since the cap 56 need not be screwed onto it. If desired, however, the cap 56 can be screwed onto it for easier assembly, but need not be removable. The rod 57 now extends further forwardly toward the cap bore, and on the forward end is permanently mounted a resilient support 60 for the needle hub 51. The support 60, for low cost and simplicity, can be a standard electrical banana type metal plug, without the usual insulating sleeve, whose wire-receiving end 61 is soldered or welded to the rod end 57. The plug itself, as shown, comprises a slightly bowed, slitted metal end 62 which is resilient and happens to be exactly sized to fit within and firmly support by a friction fit in a detachable manner the needle hub 51. The resilient end 62 of the banana plug as shown protrudes forwardly from the cap bore and thus the user can easily mount and demount the needle 50 on the plug resilient end 62. The mounted needle is shown in FIG. 8. Electrical connection is made by way of the cable wire via the metal rod 57 and the banana plug 60 to the metal needle 50 so that when the electrosurgical unit 10 is activated, RF currents can be applied to the patient via the needle point 52.

In the third embodiment depicted in FIG. 9, one form of standard handpiece can be used with a novel adaptor for mounting of the disposable needle 50. In this embodiment, the handpiece 70 is provided internally with a collect end 71 similar to the end 40 described in connection with the first embodiment, except the diameter is smaller, and the slots narrower. For example, in this third embodiment, the collet end is preferably about ½ inches long, about 3/32 inches in diameter, having about a 1/16 inch bore and four slits approximately each 1/64 inches wide. In the first embodiment, for the wider scalpel blade, the collet could have the same length, but a diameter of about 5/16 inches with a bore of about 3/16 inches and with slots of about 1/32 inches wide or slightly narrower.

In this third embodiment, the collet bore 41 is adapted to receive and clamp a cylindrical rod of about 1/16 or 3/32 inches in diameter. An adaptor or coupling piece 73 is provided, which as shown in the figure has a cylindrical rod portion 74 at the rear of the same diameter as just mentioned, and at its front a widened contoured short end 75 with a diameter chosen to receive in a friction fit the slightly resilient hub 51 of the standard needle 50. To mount the needle 50 to the handpiece, the adaptor 73 is inserted, narrow end 74 first, through the bore 39 in the removable cap 31, and then into the bore 41 of the slitted end of the collet 71. The cap 31 with metal insert, as in the first embodiment, is then rotated clockwise to cam down on the collet 71 to lock the adaptor end 74 into the collet 71. The adaptor wide end 75 will not pass through the cap bore 39 and thus will protrude from the front of the handpiece. The user then pushes the needle hub 51 onto the protruding adaptor wide end 75, and the handpiece is ready for use.

Since what is common to both the first and third embodiments is the internal collet 40, 71 of the handpiece, larger in the first embodiment to receive the wider scalpel blade 24, but smaller in the third embodiment to receive the narrow end 74 of the adaptor for the needle, it will be evident that a handpiece for holding both the scalpel blade and the needle is readily achieved by using the handpiece construction of the first embodiment and modifying the dimensions of the needle adaptor 73 so its end 74 can be mounted in the wider collet 40. This modified shape will have a larger diameter rear portion 74 for the wider collet bore 41, and a shorter overall length so that when mounted in the collet 40 the enlarged forward end 75, which has the same dimensions as before, will protrude the same distance from the handpiece front end. The adaptor piece 73 would be used when the user intends to use the needle electrode, and when the scalpel electrode is to be used, the adaptor 73 would be removed and the blade end inserted directly in the collect 40. Hence, a handpiece capable of receiving both disposable scalpels and needles is achieved in this modification.

As noted earlier, the scalpel blade can be used with or without the insulating coating 25 through the latter is preferred. The needle need not be provided with an insulating coating. Typical needle sizes are 30 gauge, ½-1 inches long; 27 gauge, ½ inches long; and 23 gauge, 1 inches long. Typical blade dimensions are overall length of about 1¾ inches, a width or height of about ¼ inches, and a thickness of slightly under 1/64 inches. The handpiece of the invention can be used with or without the patient grounding plate, though use of the latter is preferred because it provides more RF power at the electrode end affording better cutting and hemostasis.

The major benefit of the invention is to provide an inexpensive, easy-to-manufacture electrosurgical handpiece capable of using the packaged, inexpensive, sterile, disposable scalpel blades and needles readily available in the office of every physician, podiatrist or veterinarian, and thus easily available to the dentist. These disposable blades and needles, in comparison with those now available with electrosurgery equipment, are extremely low cost, typically less than 30¢ each, and thus are easily disposed of after use, yet they are made with greater precision, are extremely sharp, the blade's wider diameter produces more even, effective coagulation, the needle is typically ridged and thus stronger, and no complications need be encountered due to the absence of the need for subsequent sterilization. Thus, the handpiece of the invention which allows the use of these ubiquitous low-cost blades and needles as electrodes in an electrosurgery procedure, represents a very valuable contribution to the medical and dental arts by drastically reducing instrument expenses without sacrificing quality of performance. It is believed that use of the novel handpiece will improve the professional's ability to carry out all standard electrosurgical procedures.

FIG. 10 shows a variant of the first embodiment, in which the collet can be separated from the support rod. In this case, a metal rod 80 is secured in a central insulating collar 81 which can be screwed in by threads 82 to the rear hollow handle part 83 and functions similarly to the wall 36 in FIG. 4. The cable is connected to the end of rod 80. The forward end of the rod is threaded at 84 to receive an internally threaded hollow collet piece 85 between which is sandwiched an insulating cylindrical sleeve 86, corresponding in part to the cap 31, except that the collet end is widened at 87, and coacts with the cylindrical sleeve 86 to cam down and clamp the collet when the collet is rotated clockwise on the threaded support rod 84. The collet end has only one aligned slit for receiving the scalpel blade, and projects slightly forwardly of the sleeve 86. The device functions similarly to that depicted in FIG. 4 except that the forward protrusion of the collet end 87 allows the scalpel blade to be angled upward or downward in the vertical plane up to about 30° and clamped in that position, allowing the user to locate the blade 21 in a position more suitable for a particular procedure. Also, if desired, ribs, cradles or grooves can be provided along the surface of the handle to increase the user's tractile sense and control.

While our invention has been described in connection with specific embodiments thereof, those skilled in the art will recognize that various modifications are possible within the principles enunciated herein and thus the present invention is not to be limited to the specific embodiments disclosed.

What is claimed is:

1. A needle adaptor for use with an electrosurgical handpiece having an endface, an axis, and a central bore extending along said axis from said endface, whereby a standard disposable needle having a metal cup-shaped base with a bore may be coupled to said handpiece, said needle adaptor comprising a metal pin adapted for insertion in said central bore and a head integrally attached thereto, said head having a tapered circumferential surface adapted for insertion with friction fit in the bore of said needle base, whereby said needle can be securely coupled and electrically connected to said handpiece.

2. A handpiece for use in electrical connection with an electrosurgical unit having means for generating radio frequency current, comprising:
   (a) an elongated handle made of insulating material and having an axial bore formed therein, said handle having first and second ends;
   (b) electrical conducting means arranged in said bore and having a first terminal located near said first end for receiving radio frequency current from said electrosurgical unit and a second terminal located between said first terminal and said second end;
   (c) means for receiving a flat non-sharpened end of a standard pre-sterilized microsharp scalpel blade of the type intended for use in mechanical surgery, said receiving means being electrically connected to said second terminal; and (d) means for locking said standard pre-sterilized microsharp blade in said receiving means;

wherein said receiving means is provided with substantially parallel opposing surfaces defining a slit and extending from one end of said receiving means along a part of the axial length of said receiving means, said slit having a width substantially equal to the thickness of and a height equal to at least the height of said flat end of said standard pre-sterilized microsharp scalpel blade.

3. The handpiece as defined in claim 2, wherein said receiving means has a threaded portion, and said locking means comprises a separable part of said handle having a threaded portion by means of which said separable part is substantially fixed relative to the remainder of said handle, said threaded portions of said separable part and said receiving means being adapted for mutual threaded engagement, said separable part having a tapered bore formed therein, and said tapered bore being arranged such that said one end of said receiving means is compressed as said separable part is rotated in one direction during said threaded engagement and said one end of said receiving end is loosened as said locking means is rotated in an opposite direction during said threaded engagement.

4. The handpiece as defined in claim 2, wherein said one end of said receiving means is arranged near said second end of said handle.

5. The handpiece as defined in claim 2, wherein said locking means comprises a separable part of said handle, is made of insulating material and has a bore for receiving said receiving means, said receiving means and said second terminal having threaded portions for mutual threaded engagement, and said receiving means further having a tapered outer circumferential surface at said one end, said tapered surface being adapted to engage the bore of said locking means during rotation of said receiving means in one direction during said threaded engagement such that said one end is compressed, whereby said gap width is decreased for locking said standard pre-sterilized microsharp scalpel blade between said opposing surfaces.

6. A handpiece for use in electrical connection with an electrosurgical unit having means for generating radio frequency current, comprising:

(a) an elongated handle made of insulating material and having an axial bore formed therein, said handle having first and second ends;

(b) electrical conducting means arranged in said bore and having a first terminal located near said first end for receiving radio frequency current from said electrosurgical unit and a second terminal located between said first terminal and said second end;

(c) means for receiving a flat non-sharpened end of a standard pre-sterilized microsharp scalpel blade of the type intended for use in mechanical surgery, said receiving means being electrically connected to said second terminal; and (d) means for locking said standard pre-sterilized microsharp scalpel blade in said receiving means;

wherein said receiving means is provided with a first pair of substantially parallel opposing surfaces defining a first slit and extending from one end of said receiving means along a part of the axial length of said receiving means, and a second pair of substantially parallel opposing surfaces defining a second slit and extending from one end of said receiving means along a part of the axial length of said receiving means, said first and second slits being aligned and having a width substantially equal to the thickness of said flat end of said standard pre-sterilized microsharp scalpel blade.

7. The handpiece as defined in claim 6, wherein said receiving means is made of metal and has an axis, an outer surface, and an endface substantially transverse to said axis, said first and second slits being radially directed and said receiving means having an axial central bore which communicates with said first and second radial slits, said radial slits and said central bore extending from said endface along only a portion of the axial length of said receiving means, said portion being sufficiently long to enable flexure of the portions of said one end separated by said radial slits and axial bore, whereby said opposing surfaces can be relatively displaced.

8. The handpiece as defined in claim 7, wherein the width of said gap between said opposing surfaces is decreased in response to the application of radially inwardly directed forces by said locking means.

9. A handpiece for use with electrosurgical equipment supplying RF current in combination with a standard presterilized disposable scalpel blade, comprising:

(a) an elongated insulated handle having a hollow interior and first and second ends, (b) an insulated electrical wire entering the first end of the handle, (c) an electrically conductive structure mounted within the handle at its second end and electrically connected to the wire, said structure including within the handle an elongated metal part having adjacent the said handle second end a collet and further including a threaded portion, (d) said handle at its second end having an outer portion having on its interior a portion configured such that relative rotational movement using the threaded portion can take place between said outer portion and said collet so that when rotation occurs in one direction the outer portion tightens up on the collet, and when rotation occurs in the opposite direction the outer portion loosens up on the collet, (e) said scalpel blade comprising a thin flat one-piece plate-like metal member having a front and a rear, said member having at its front a surgically-sharpened edge and at its rear a flat mounting portion containing a slot adapted for removable mounting of the blade on a manual handle for use in a non-electrosurgical procedure, (f) said collet comprising radial slits configured to removably receive and hold the flat rear mounting portion of said scalpel blade when inserted therein, (g) said handle being configured such that when the rear mounting portion of the scalpel blade is inserted in the collet and rotation is effected to tighten up on the collet, the blae is locked to the collet and handle and electrically connected to the electrical wire, and when rotation is effected to loosen up on the collet the blade is unlocked from the collet and handle and may be removed by a user from the handle, said sharpened edge of the scalpel blade protruding from the handle second end when the blade is locked therein, whereby standard pre-sterilized disposable scalpel blades originally designed for use in manual handles in non-electrosurgical procedures can be removably mounted and selectively locked in the said insulated handle which when connected to electrosurgical equipment will enable a user to conduct an electrosurgical procedure with the aid of RF current with the scalpel blade surgically-sharpened edge functioning as the electrosurgical electrode allowing tissue cutting by the user together with hemostasis or without the aid of RF current allowing tissue cutting alone as selected by the user.

10. The combination as claimed in claim 9 wherein the slits in the collet are aligned, and the scalpel blade consists essentially of stainless steel metal.

11. The combination as claimed in claim 10 wherein the collet comprises a receiving face for the blade end that consists of a single straight slit.

12. The combination as claimed in claim 11 wherein the receiving face of the collet extends from an outwardly-tapered portion.

* * * * *